United States Patent
Edwards et al.

(10) Patent No.: US 6,503,480 B1
(45) Date of Patent: *Jan. 7, 2003

(54) AERODYNAMICALLY LIGHT PARTICLES FOR PULMONARY DRUG DELIVERY

(75) Inventors: David A. Edwards, Boston, MA (US); Giovannia Caponetti, Piacenza (IT); Jeffrey S. Hrkach, Somerville, MA (US); Noah Lotan, Haifa (IL); Justin Hanes, Baltimore, MD (US); Abdell Aziz Ben-Jebria, State College, PA (US); Robert S. Langer, Newton, MA (US)

(73) Assignees: Massachusetts Institute of Technology, Cambridge, MA (US); The Penn State Research Foundation, University Park, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/194,068
(22) PCT Filed: May 23, 1997
(86) PCT No.: PCT/US97/08895
§ 371 (c)(1), (2), (4) Date: Apr. 8, 1999
(87) PCT Pub. No.: WO97/44013
PCT Pub. Date: Nov. 27, 1997

(51) Int. Cl.$^7$ ................................................. A61K 9/12
(52) U.S. Cl. ............................ 424/45; 424/46; 424/489
(58) Field of Search ............................. 424/45, 489, 46

(56) References Cited

U.S. PATENT DOCUMENTS 4,590,206 A  5/1986  Forrester et al.
4,741,872 A  5/1988  De Luca et al.

(List continued on next page.)

FOREIGN PATENT DOCUMENTS

EP    072 046       2/1983
EP    0072046    *  2/1983

(List continued on next page.)

OTHER PUBLICATIONS

Hrkach, et al., "Synthesis of Poly(L-lactic acid-co-L-Iysine) Graft Copolymers," *Macromolecules*, 28:4736–4739, 1995.

(List continued on next page.)

*Primary Examiner*—Raj Bawa
(74) *Attorney, Agent, or Firm*—Hamilton, Brook, Smith & Reynolds, P.C.

(57) ABSTRACT

Improved aerodynamically light particles for delivery to the pulmonary system, and methods for their preparation and administration are provided. In a preferred embodiment, the aerodynamically light particles are made of a biodegradable material and have a tap density less than 0.4 g/cm$^3$ and a mass mean diameter between 5 μm and 30 μm. The particles may be formed of biodegradable mat as biodegradable polymers. For example, the particles may be formed of a functionalized polyester graft copolymer consisting of a linear α-hydroxy-acid polyester backbone having at least one amino acid group incorporated therein and at least one poly(amino acid) side chain extending from an amino acid group in the polyester backbone. In one embodiment, aerodynamically light particles having a large mean diameter, for example greater than 5 μm, can be used for enhanced delivery of a therapeutic or diagnostic agent to the alveolar region of the lung. The aerodynamically light particles optionally can incorporate a therapeutic or diagnostic agent, and may be effectively aerosolized for administration to the respiratory tract to permit systemic or local delivery of wide variety of incorporated agents.

35 Claims, 4 Drawing Sheets

U.S. PATENT DOCUMENTS

| | | | |
|---|---|---|---|
| 4,818,542 A | | 4/1989 | De Luca et al. |
| 4,904,479 A | | 2/1990 | De Luca et al. |
| 5,069,936 A | | 12/1991 | Yen |
| 5,145,684 A | * | 9/1992 | Liversidge et al. |
| 5,160,745 A | | 11/1992 | De Luca et al. |
| 5,260,306 A | * | 11/1993 | Boardman et al. |
| 5,506,203 A | | 4/1996 | Bäckström et al. |
| 5,518,998 A | | 5/1996 | Bäckström et al. |
| 5,612,053 A | | 3/1997 | Baichwal et al. |
| 5,642,728 A | | 7/1997 | Anderson et al. |
| 5,690,954 A | | 11/1997 | Illum |
| 5,707,644 A | | 1/1998 | Illum |
| 5,795,594 A | | 8/1998 | York et al. |
| 5,804,212 A | * | 9/1998 | Illum |
| 5,830,853 A | | 11/1998 | Bäckström et al. |
| 5,851,453 A | | 12/1998 | Hanna et al. |
| 5,855,913 A | * | 1/1999 | Hanes et al. |
| 5,874,064 A | * | 2/1999 | Edwards et al. |
| 5,985,309 A | | 11/1999 | Edwards et al. |
| 5,997,848 A | | 12/1999 | Patton et al. |
| 6,063,138 A | | 5/2000 | Hanna et al. |

FOREIGN PATENT DOCUMENTS

| | | |
|---|---|---|
| WO | 97/36574 | 3/1996 |
| WO | 99/16419 | 4/1999 |
| WO | 99/16420 | 4/1999 |
| WO | 99/16421 | 4/1999 |
| WO | 99/16422 | 4/1999 |

OTHER PUBLICATIONS

Hrkach, et al., Poly(L–Lactic acid–co–amino acid) Graft Copolymers: A Class of Functional Biodegradable Biomaterials: in Hydrogels and Biodegradable Polymers for Bio-applications. ACS Symposium Series No. 627, Raphael M. Ottenbrite et al., Eds., American Chemical Society, Chapter 8, pp 93–101, 1996.

Komanda, et al., Intratracheal Delivery of Peptide and Protein Agents: Absorption of Solution and Dry Powder by Rat Lung,: *J. Pharm. Sci.*, 83(6):863–867, 1994.

Edwards, "The Macrotransport of Aerosol Particles in the Lung: Aerosol Deposition Phenomena," *J. Aerosol Sci.*, 26:293–317, 1995.

Newman, S., "Aerosol Deposition Considerations in Inhalation Therapy," *Chest*, 88:152S–160S, 1985.

Langer, "New Methods of Drug Delivery", *Science*, 249:1527–1533, 1990.

Gonda, "Aerosols for Delivery of Therapeutic and Diagnostic Agents to the Respiratory Tract," in *Critical Reviews in Therapeutic Drug Carrier Systems*, 6:273–313, 1990.

Gonda, "Preface. Major Issues and Future Prospects in the Delivery of Therapeutic and Diagnostic Agents to the Respiratory Tract," *Adv. Drug Del. Rev.* 5:1–9, 1990.

Gonda, "Physico–chemical Principles in Aerosol Delivery," in Topics in Pharmaceutical Sciences 1991, Crommelin, D.J. and K.K. Midha, Eds., Medpharm Scientific Publishers, Stuttgart, pp. 95–117, 1992.

Gonda, "Targeting by Deposition," in Pharmaceutical Inhalation Aerosol Technology (ed. A.J. Hickey), Marcel Dekkar Inc., New York, 1992.

Zanen, P., et al., "The Optimal Particle Size for Parasympathicolytic Aerosols in Mild Asthmatics," *Inter. J. of Pharm.,* 114:111–115 (1995).

Heyder and Rudolf, "Mathematical Models of Particle Deposition in the Human Respiratory Tract," *J. Aerosol Sci.,* 15: 697–707, 1984.

Heyder, et al., "Total Deposition of Aerosol Particles in the Human Respiratory Tract for Nose and Mouth Breathing," *J. Aerosol Sci.,* 6:311–328, 1975.

Hicky, et al., "Use of Particle Morphology to Influence the Delivery of Drugs From Dry Powder Aerosols," *J. Biopharmaceutical Sci.,* 3(1/2):107–113, 1992.

Edwards, et al., "Large Porous Particles for Pulmonary Drug Delivery," *Science 276*:1868–1871, 1997.

Masinde and Hickey, "Aerosolized Aqueous Suspensions at Poly(L–lactic Acid) Microspheres," *Int. J. Pharmaceutics,* 100:123–131, 1993.

Wichert B. and Rohdewald P., "Low Molecular Weight PLA: A Suitable Polymer for Pulmonary Administered Microparticles?," *J. Microencapsulation Vol. 10(2)*:195–207, 1993.

French, Edwards. and Niven, "The Influence of Formulation of Emission, Deaggregation and Deposition of Dry Powders for Inhalation," *J. Aerosol Sci.,* 27:769–783, 1996.

Tabata and Ikada, "Effect of Size and Surface Charge of Polymer Microspheres on Their Phagocytosis by Macrophage," *J. Biomed. Mater. Res.,* 22:837, 1988.

Timsina, et al., "Drug Delivery to the Respiratory Tract Using Dry Powder Inhalers," *Int. J. Pharm.,* 101:1–13, 1994.

Zeng, et al., "The Controlled Delivery of Drugs to the Lung," *Intern. J. of Pharm. 124*:149–164, 1995.

Ménache, et al., "Particle Inhalability Curves for Humans and Small Laboratory Animals," *Ann Occup. Hyg. Vol. 39*(*3*):317–328, 1995.

Mathiowitz, et al., "Novel Microcapsules for Delivery Systems," *Reactive Polymers,* 6:275–283, 1987.

Mathiowitz, et al., "Morphology of Polyanhydride Microsphere Delivery Systems," *Scanning Microscopy,* vol. 4(2):329–340, 1990.

Mathiowitz, et al., "Polyanhydride Microspheres. IV. Morphology and Characterization of Systems Made by Spray Drying," *J. of Appl. Polymer Sci.,* vol. 45:125–134, 1992.

Martonen, T.B., "Mathematical Model for the Selective Disposition of Inhaled Pharmeceuticals," *J. of Pharm. Sci.,* vol. 82(12):1191–1199, 1993.

Clark, A. and Egan, M., "Modelling the Deposition of Inhaled Powdered Drug Aerosols," *J. Aerosol Sci.,* vol. 25(1):175–186, 1994.

Colthorpe, et al., "The Pharmacokinetics of Pulmonary–Delivered Insulin: A Comparison of Intratracheal and Aerosol Administration to the Rabbit," *Pharmaceutical Research,* vol. 9(6):764–768, 1992.

Kwok, et al., "Production of 5–15 μm Diameter Alginate–Polylysine Microcapsules by an Air–Atomization Technique," *Pharmaceutical Research,* vol. 8(3):341–344, 1991.

* cited by examiner

AERODYNAMICALLY LIGHT PARTICLES FOR PULMONARY DRUG DELIVERY

CROSS REFERENCE TO RELATED APPLICATION

This application is the National Stage Application under 35 U.S.C § 371(c) of PCT US97/08895 filed on May 23, 1997 and claiming priority to U.S. application Ser. No. 08/739,308, filed on Oct. 29, 1996, now U.S. Pat. No. 5,874,064, and of U.S. application Ser. No. 08/655,570, filed on May 24, 1996 now abandoned.

BACKGROUND OF THE INVENTION

The present application relates generally to biodegradable particles of low density and large size for delivery to the pulmonary system.

Biodegradable particles have been developed for the controlled-release and delivery of protein and peptide drugs. Langer, R., *Science*, 249: 1527–1533 (1990). Examples include the use of biodegradable particles for gene therapy (Mulligan, R. C. *Science*, 260: 926–932 (1993)) and for 'single-shot' immunization by vaccine delivery (Eldridge et al., *Mol. Iminunol.*, 28: 287–294 (1991)).

Aerosols for the delivery of therapeutic agents to the respiratory tract have been developed. Adjei, A. and Garren, *J. Pharm.* Res. 7, 565–569 (1990); and Zanen, P. and Lamm, J. -W. J. *Int. J. Pharm.* 114, 111–115 (1995). The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchioli which then lead to the ultimate respiratory zone, the alveoli, or deep lung. Gonda, I. "Aerosols for delivery of therapeutic and diagnostic agents to the respiratory tract," in *Critical Reviews in Therapeutic Drug Carrier Systems* 6:273–313, 1990. The deep lung, or alveoli, are the primary target of inhaled therapeutic aerosols for systemic drug delivery.

Inhaled aerosols have been used for the treatment of local lung disorders including asthma and cystic fibrosis (Anderson et al., *Am. Rev. Respir. Dis.*, 140: 1317–1324 (1989)) and have potential for the systemic delivery of peptides and proteins as well (Patton and Platz, *Advanced Drug Delivery Reviews*, 8:179–196 (1992)). However, pulmonary drug delivery strategies present many difficulties for the delivery of macromolecules; these include protein denaturation during aerosolization, excessive loss of inhaled drug in the oropharyngeal cavity (often exceeding 80%), poor control over the site of deposition, irreproducibility of therapeutic results owing to variations in breathing patterns, the often too-rapid absorption of drug potentially resulting in local toxic effects, and phagocytosis by lung macrophages.

Considerable attention has been devoted to the design of therapeutic aerosol inhalers to improve the efficiency of inhalation therapies. Timsina et. al.,*Int. J. Pharm.* 101, 1–13 (1995); and Tansey, I. P., *Spray, Technol. Market* 4, 26–29 (1994). Attention has also been given to the design of dry powder aerosol surface texture, regarding particularly the need to avoid particle aggregation, a phenomenon which considerably diminishes the efficiency of inhalation therapies. French, D. L., Edwards, D. A. and Niven, R. W., *J. Aerosol Sci.* 27, 769–783 (1996). Attention has not been given to the possibility of using large particle size (greater than 5 $\mu$m) as a means to improve aerosolization efficiency, despite the fact that intraparticle adhesion diminishes with increasing particle size. French, D. L., Edwards, D. A. and Niven, R. W. *J. Aerosol Sci.* 27, 769–783 (1996). This is because particles of standard mass density (mass density near 1 g/cm$^3$) and mean diameters greater than 5 $\mu$m are known to deposit excessively in the upper airways or in the inhaler device. Heyder, J. et al., *J. Aerosol Sci.*, 17: 811–825 (1986). For this reason, dry powder aerosols for inhalation therapy are generally produced with mean diameters primarily in the range of less than 5 $\mu$m. Ganderton. D., *J. Biopharnaceutical Sciences* 3:101–105 (1992): and Gonda, I "Physico-Chemical Principles in Aerosol Delivery," in *Topics in Pharmaceutical Sciences* 1991, Crommelin, D. J. and K. K. Midha, Eds., Medpharm Scientific Publishers, Stuttgart, pp. 95–115, 1992. Large "carrier" particles (containing no drug) have been co-delivered with therapeutic aerosols to aid in achieving efficient aerosolization among other possible benefits. French, D. L., Edwards, D. A. and Niven, R. W. *J. Aerosol Sci.* 27, 769–783 (1996).

Local and systemic inhalation therapies can often benefit from a relatively slow controlled release of the therapeutic agent. Gonda, I., "Physico-chemical principles in aerosol delivery," in: *Topics in Pharmaceutical Sciences* 1991, D. J. A. Crommelin and K. K. Midha, Eds., Stuttgart: Medpharm Scientific Publishers, pp. 95–117, (1992). Slow release from a therapeutic aerosol can prolong the residence of an administered drug in the airways or acini, and diminish the rate of drug appearance in the bloodstream. Also, patient compliance is increased by reducing the frequency of dosing. Langer, R., *Science*, 249:1527–1533 (1990); and Gonda, I. "Aerosols for delivery of therapeutic and diagnostic agents to the respiratory tract," in *Critical Reviews in Therapeutic Drug Carrier Systems* 6:273–313, (1990).

The human lungs can remove or rapidly degrade hydrolytically cleavable deposited aerosols over periods ranging from minutes to hours. In the upper airways, ciliated epithelia contribute to the "mucociliary escalator" by which particles are swept from the airways toward the mouth. Pavia, D. "Lung Mucociliary Clearance," in *Aerosols and the Lung: Clinical and Experimental Aspects*, Clarke, S. W. and Pavia, D., Eds., Butterworths, London, 1984. Anderson et al., *Am. Rev. Respir. Dis.*, 140: 1317–1324 (1989). In the deep lungs, alveolar macrophages are capable of phagocytosing particles soon after their deposition. Warheit, M. B. and Hartsky, M. A., *Microscopy Res. Tech.* 26: 412–422 (1993); Brain, J. D., "Physiology and Pathophysiology of Pulmonary Macrophages," in *The Reticuloendothelial System*, S. M. Reichard and J. Filkins, Eds., Plenum, New York, pp. 315–327, 1985; Dorries. A. M. and Valberg, P. A., *Am. Rev. Resp. Disease* 146, 831–837 (1991); and Gehr, P. et al. *Microscopy Res. and Tech*. 26, 423–436 (1993). As the diameter of particles exceeds 3 $\mu$m, there is increasingly less phagocytosis by macrophages. Kawaguchi, H. et al., *Biomaterials* 7: 61–66 (1986); Krenis, L. J. and Strauss, B., *Proc. Soc. Exp. Med.*, 107:748–750 (1961); and Rudt, S. and Muller, R. H., *J. Contr. Rel.*, 22: 263–272 (1992). However, increasing the particle size also minimizes the probability of particles (possessing standard mass density) entering the airways and acini due to excessive deposition in the oropharyngeal or nasal regions. Heyder, J. et al.,*J. Aerosol Sci.*, 17: 811–825 (1986). An effective dry-powder inhalation therapy for both short and long term release of therapeutics, either for local or systemic delivery, requires a powder that displays minimum aggregation and is capable of avoiding or suspending the lung's natural clearance mechanisms until drugs have been effectively delivered.

There is a need for improved inhaled aerosols for pulmonary delivery of therapeutic agents which are capable of delivering the drug in an effective amount into the airways or the alveolar zone of the lung. There further is a need for the development of drug carriers for use as inhaled aerosols which are biodegradable and are capable of controlled release of drug within the airways or in the alveolar zone of the lung.

It is therefore an object of the present invention to provide improved carriers for the pulmonary delivery of therapeutic and diagnostic agents. It is a further object of the invention to provide inhaled aerosols which are effective carriers for delivery of therapeutic or diagnostic agents to the deep lung. It is another object of the invention to provide carriers for pulmonary delivery which avoid phagocytosis in the deep lung. It is a further object of the invention to provide carriers for pulmonary delivery which are capable of biodegrading and optionally releasing incorporated agents at a controlled rate.

SUMMARY OF THE INVENTION

Improved aerodynamically light particles for delivery to the pulmonary system, and methods for their preparation and administration are provided. In a preferred embodiment, the particles are made of a biodegradable material, have a tap density less than 0.4 g/cm$^3$ and a mean diameter between 5 $\mu$m and 30 $\mu$m. In one embodiment, for example, at least 90% of the particles have a mean diameter between 5 $\mu$m and 30 $\mu$m. The particles may be formed of biodegradable materials such as biodegradable synthetic polymers, proteins, or other water-soluble materials such as certain polysaccharides. For example, the particles may be formed of a functionalized polyester graft copolymer with a linear $\alpha$-hydroxy-acid polyester backbone with at least one amino acid residue incorporated per molecule therein and at least one poly(amino acid) side chain extending from an amino acid group in the polyester backbone. Other examples include particles formed of water-soluble excipients, such as trehalose or lactose, or proteins, such as lysozyme or insulin. The particles can be used for delivery of a therapeutic or diagnostic agent to the airways or the alveolar region of the lung. The particles may be effectively aerosolized for administration to the respiratory tract and can be used to systemically or locally deliver a wide variety of incorporated agents. The particles incorporating an agent can optionally be co-delivered with larger carrier particles, not carrying an incorporated agent, which have, for example, a mean diameter ranging between about 50 $\mu$m and 100 $\mu$m.

DETAILED DESCRIPTION OF THE INVENTION

Aerodynamically light, biodegradable particles for improved delivery to the respiratory tract are provided. The particles can incorporate a therapeutic or diagnostic agent, and can be used for controlled systemic or local delivery of the agent to the respiratory tract via aerosolization. In a preferred embodiment, the particles have a tap density less than about 0.4 g/cm$^3$. Features of the particle which can contribute to low tap density include irregular surface texture and porous structure. Administration of the low density particles to the lung by aerosolization permits deep lung delivery of relatively large diameter therapeutic aerosols, for example, greater than 5 $\mu$m in mean diameter. A rough surface texture also can reduce particle agglomeration and provide a highly flowable powder, which is ideal for aerosolization via dry powder inhaler devices, leading to lower deposition in the mouth, throat and inhaler device.

Density and Size of Aerodynamically Light Particles

Particle Size

The mass mean diameter of the particles can be measured using a Coulter Counter. The aerodynamically light particles are preferably at least about 5 microns in diameter. The diameter of particles in a sample will range depending upon depending on factors such as particle composition and methods of synthesis. The distribution of size of particles in a sample can be selected to permit optimal deposition within targeted sites within the respiratory tract.

The particles may be fabricated or separated, for example. by filtration, to provide a particle sample with a preselected size distribution. For example, greater than 30%, 50%, 70%, or 80% of the particles in a sample can have a diameter within a selected range of at least 5 $\mu$m. The selected range within which a certain percentage of the particles must fall may be, for example, between about 5 and 30 $\mu$m, or optionally between 5 and 15 $\mu$m. In one preferred embodiment, at least a portion of the particles have a diameter between about 9 and 11 $\mu$m. Optionally, the particle sample also can be fabricated wherein at least 90%, or optionally 95% or 99%, have a diameter within the selected range. The presence of the higher proportion of the aerodynamically light, larger diameter (at least about 5 $\mu$m) particles in the particle sample enhances the delivery of therapeutic or diagnostic agents incorporated therein to the deep lung.

In one embodiment, in the particle sample, the interquartile range may be 2 $\mu$m, with a mean diameter for example of 7.5, 8.0, 8.5, 9.0, 9.5, 10.0, 10.5, 11.0, 11.5, 12.0, 12.5, 13.0 or 13.5 $\mu$m. Thus. for example, at least 30%, 40%, 50% or 60% of the particles may have diameters within the selected ranges of 5.5–7.5 $\mu$m, 6.0–8.0 $\mu$m, 6.5–8.5 $\mu$m, 7.0–9.0 $\mu$m, 7.5–9.5 $\mu$m, 8.0–10.0 $\mu$m, 8.5–10.5 $\mu$m, 9.0–11.0 $\mu$m, 9.5–11.5 $\mu$m, 10.0–12.0 $\mu$m, 10.5–12.5$\mu$m, 11.0–13.0 $\mu$m, 11.5–13.5 $\mu$m, 12.0–14.0 $\mu$m, 12.5–14.5 $\mu$m or 13.0–15.0 $\mu$m. Preferably the above-listed percentages of particles have diameters within a 1 $\mu$m range, for example, 6.0–7.0 $\mu$m, 10.0–11.0 $\mu$m or 13.0–14.0 $\mu$m.

Particles having a tap density less than about 0.4 g/cm$^3$ and a mean diameter of at least about 5 $\mu$m are more capable of escaping inertial and gravitational deposition in the oropharyngeal region than smaller or more dense particles, and are targeted to the airways of the deep lung. The use of larger particles (mean diameter greater than 5 $\mu$m) is advantageous since they are able to aerosolize more efficiently than smaller, denser particles such as those currently used for inhalation therapies.

In comparison to smaller, denser particles, the larger (greater than 5 $\mu$m) aerodynamically light particles also can potentially more successfully avoid phagocytic engulfment by alveolar macrophages and clearance from the lungs, due to size exclusion of the particles. from the phagocytes' cytosolic space. For particles of statistically isotropic shape (on average, particles of the powder possess no distinguishable orientation), such as spheres with rough surfaces, the particle envelope volume is approximately equivalent to the volume of cytosolic space required within a macrophage for complete particle phagocytosis.

Aerodynamically light particles thus are capable of a longer term release of an incorporated diagnostic or therapeutic agent than smaller, denser particles. Following inhalation, aerodynamically light biodegradable particles can deposit in the lungs (due to their relatively low tap density), and subsequently undergo slow degradation and drug release, without the majority of the particles being phagocytosed by alveolar macrophages. The agent can be delivered relatively slowly into the alveolar fluid, and at a controlled rate into the blood stream, minimizing possible toxic responses of exposed cells to an excessively high concentration of the agent. The aerodynamically light particles thus are highly suitable for inhalation therapies, particularly in controlled release applications.

The particles may be fabricated with the appropriate material, surface roughness, diameter and tap density for localized delivery to selected regions of the respiratory tract such as the deep lung or upper airways. For example, higher density or larger particles may be used for upper airway delivery, or a mixture of different sized particles in a sample, provided with the same or different incorporated agent may be administered to target different regions of the lung in one administration.

Particle Density and Deposition

The particles have a diameter of at least about 5 $\mu$m and optionally incorporate a therapeutic or diagnostic agent. The particles are preferably aerodynamically light. As used herein, the phrase "aerodynamically light particles" refers to particles having a tap density less than about 0.4 g/cm$^3$. The tap density of particles of a dry powder may be obtained using a Geo Phy™ (Micrometrics Instrument Corp., Norcross, Ga. 30093). Tap density is a standard measure of the envelope mass density. The envelope mass density of an isotropic particle is defined as the mass of the particle divided by the minimum sphere envelope volume within which it can be enclosed.

Inertial impaction and gravitational settling of aerosols are predominant deposition mechanisms in the airways and acini of the lungs during normal breathing conditions. Edwards, D. A., J. Aerosol Sci. 26:293–317 (1995). The importance of both deposition mechanisms increases in proportion to the mass of aerosols and not to particle (or envelope) volume. Since the site of aerosol deposition in the lungs is determined by the mass of the aerosol (at least for particles of mean aerodynamic diameter greater than approximately 1 $\mu$m), diminishing the tap density by increasing particle surface irregularities and particle porosity permits the delivery of larger particle envelope volumes into the lungs, all other physical parameters being equal.

The low tap density particles have a small aerodynamic diameter in comparison to the actual envelope sphere diameter. The aerodynamic diameter, $d_{aer}$, is related to the envelope sphere diameter, d (Gonda, I., "Physico-chemical principles in aerosol delivery," in *Topics in Pharmaceutical Sciences* 1991 (eds. D. J. A. Crommelin and K. K. Midha), pp. 95–117, Stuttgart: Medpharm Scientific Publishers. 1992) by the formula:

$$d_{aer}=d\sqrt{\rho}$$

where the envelope mass $\rho$ is in units of g/cm$^3$. Maximal deposition of monodisperse aerosol particles in the alveolar region of the human lung (approximately 60%) occurs for an aerodynamic diameter of approximately $d_{aer}$=3 $\mu$m. Heyder, J. et al., J. Aerosol Sci., 17: 811–825 (1986). Due to their small envelope mass density, the actual diameter d of aerodynamically light particles comprising a monodisperse inhaled powder that will exhibit maximum deep-lung deposition is:

$$d=3/\sqrt{\rho}\mu m \text{ (where } \rho<1 \text{ g/cm}^3\text{)};$$

where d is always greater than 3 $\mu$m. For example, aerodynamically light particles that display an envelope mass density, $\rho$=0.1 g/cm$^3$. will exhibit a maximum deposition for particles having envelope diameters as large as 9.5 $\mu$m. The increased particle size diminishes interparticle adhesion forces. Visser, J., *Powder Technology*, 58:1–10. Thus, large particle size increases efficiency of aerosolization to the deep lung for particles of low envelope mass density, in addition to contributing to lower phagocytic losses.

Particle Materials

The aerodynamically light particles preferably are biodegradable and biocompatible, and optionally are capable of biodegrading at a controlled rate for release of an incorporated thereapeutic or diagnostic agent. The particles can be made of any material which is capable of forming a particle having a tap density less than about 0.4 g/cm$^3$. Both inorganic and organic materials can be used. Other non-polymeric materials (e.g. fatty acids) may be used which are capable of forming aerodynamically light particles as defined herein. Different properties of the particle can contribute to the aerodynamic lightness including the composition forming the particle, and the presence of irregular surface structure or pores or cavities within the particle.

Polymeric Particles

The particles may be formed from any biocompatible, and preferably biodegradable polymer, copolymer, or blend, which is capable of forming particles having a tap density less than about 0.4 g/cm$^3$.

Surface eroding polymers such as polyanhydrides may be used to form the aerodynamically light particles. For example, polyanhydrides such as poly[(ρ-carboxyphenoxy)-hexane anhydride] (PCPH) may be used. Biodegradable polyanhydrides are described, for example, in U.S. Pat. No. 4,857,311.

In another embodiment, bulk eroding polymers such as those based on polyesters, including poly(hydroxy acids), can be used. Preferred poly(hydroxy acids) are polyglycolic acid (PGA), polylactic acid (PLA) and copolymers and coblends thereof. In one embodiment, the polyester has incorporated therein a charged or functionalizable group such as an amino acid.

Other polymers include polyamides, polycarbonates, polyalkylenes such as polyethylene, polypropylene, poly (ethylene glycol), poly(ethylene oxide), poly(ethylene terephthalate), poly vinyl compounds such as polyvinyl alcohols, polyvinyl ethers, and polyvinyl esters, polymers of acrylic and methacrylic acids, celluloses and other polysaccharides, and peptides or proteins, or copolymers or blends thereof. Polymers may be selected with or modified to have the appropriate stability and degradation rates in vivo for different controlled drug delivery applications.

Polyester Graft Copolymers

In one preferred embodiment, the aerodynamically light particles are formed from functionalized polyester graft copolymers, as described in Hrkach et al., *Macromolecules*, 28:4736–4739 (1995); and Hrkach et al., "Poly(L-Lactic acid-co-amino acid) Graft Copolymers: A Class of Functional Biodegradable Biomaterials" in *Hydrogels and Biodegradable Polymers for Bioapplications*, ACS Symposium Series No. 627, Raphael M. Ottenbrite et al., Eds., μmerican Chemical Society, Chapter 8, pp. 93–101, 1996. The functionalized graft copolymers are copolymers of polyesters, such as poly(glycolic acid) or poly(lactic acid), and another polymer including functionalizable or ionizable groups, such as a poly(amino acid). In a preferred embodiment, comb-like graft copolymers are used which include a linear polyester backbone having amino acids incorporated therein, and poly(amino acid) side chains which extend from the amino acid residues in the polyester backbone. The polyesters may be polymers of α-hydroxy acids such as lactic acid, glycolic acid, hydroxybutyric acid and hydroxyvaleric acid, or derivatives or combinations thereof. The polymers can include ionizable side chains, such as polylysine and polyaniline. Other ionizable groups, such as amino or carboxyl groups, may be incorporated into the polymer. covalently or noncovalently, to enhance surface roughness and porosity.

An exemplary polyester graft copolymer is poly(lactic acid-colysine-graft-lysine) (PLAL-Lys), which has a polyester backbone consisting of poly(L-lactic acid-co- L-lysine) (PLAL), and grafted polylysine chains. PLAL-Lys is a comb-like graft copolymer having a backbone composition, for example, of 98 mol % lactic acid and 2 mol % lysine and poly(lysine) side chains extending from the lysine sites of the backbone.

PLAL-Lys may be synthesized as follows. First, the PLAL copolymer consisting of L-lactic acid units and approximately 1–2% N ϵ carbobenzoxy-L-lysine (Z-L-lysine) units is synthesized as described in Barrera et al., *J. Am. Chem. Soc.*, 115:11010 (1993). Removal of the Z protecting groups of the randomly incorporated lysine groups in the polymer chain of PLAL yields the free E-amine which can undergo further chemical modification. The use of the poly(lactic acid) copolymer is advantageous since it biodegrades into lactic acid and lysine, which can be processed by the body. The existing backbone lysine groups are used as initiating sites for the growth of poly(amino acid) side chains.

The lysine ϵ-amino groups of linear poly(L-lactic acid-co-L-lysine) copolymers initiate the ring opening polymerization of an amino acid N-ϵ carboxyanhydride (NCA) to produce poly(L-lactic acid-co-amino acid) comb-like graft copolymers. In a preferred embodiment, NCAs are synthesized by reacting the appropriate amino acid with triphosgene. Daly et al., *Tetrahedron Lett.*, 29:5859 (1988). The advantage of using triphosgene over phosgene gas is that it is a solid material, and therefore, safer and easier to handle. It also is soluble in THF and hexane so any excess is efficiently separated from the NCAs.

The ring opening polymerization of amino acid N-carboxyanhydrides (NCAs) is initiated by nucleophilic initiators such as amines, alcohols, and water. The primary amine initiated ring opening polymerization of NCAs allows efficient control over the degree of polymerization when the monomer to initiator ratio (M/I) is less than 150. Kricheldorf, H. R. in *Models of Biopolymers by Ring-Opening Polymerization*, Penczek, S., Ed., CRC Press, Boca Raton, 1990. Chapter 1; Kricheldorf, H. R. *α-Aminoacid-N-Carboxy-Anhydrides and Related Heterocycles*, Spriner-Verlag, Berlin, 1987; and Imanishi, Y. in *Ring-Opening Polymerization*, Ivin, K. J. and Saegusa, T., Eds., Elsevier, London, 1984, Volume 2, Chapter 8. Methods for using lysine ϵ-amino groups as polymeric initiators for NCA polymerizations are described in the art. Sela, M. et al., *J. Am. Chem. Soc.*, 78: 746 (1956).

In the reaction of an amino acid NCA with PLAL, the nucleophilic primary ϵ-amino group of the lysine side chain attacks C-5 of the NCA. This leads to ring opening to form an amide linkage, accompanied by evolution of a molecule of $CO_2$. The amino group formed by the evolution of $CO_2$ propogates the polymerization by attacking subsequent NCA molecules. The degree of polymerization of the poly (amino acid) side chains, the amino acid content in the resulting graft copolymers and the physical and chemical characteristics of the resulting copolymers can be controlled by adjusting the ratio of NCA to lysine ϵ-amino groups in the PLAL polymer, for example, by adjusting the length of the poly(amino acid) side chains and the total amino acid content.

The poly(amino acid) side chains grafted onto or incorporated into the polyester backbone can include any amino acid. such as aspartic acid, alanine or lysine, or mixtures thereof. The functional groups present in the amino acid side chains, which can be chemically modified, include amino, carboxylic acid, thiol, guanido, imidazole and hydroxyl groups. As used herein, the term "amino acid" includes natural and synthetic amino acids and derivatives thereof. The polymers can be prepared with a range of side chain lengths. The side chains preferably include between 10 and 100 amino acids, and have an overall amino acid content between 7 and 72%. However, the side chains can include more than 100 amino acids and can have an overall amino acid content greater than 72%, depending on the reaction conditions. Poly(amino acids) can be grafted to the PLAL backbone in any suitable solvent. Suitable solvents include polar organic solvents such as dioxane, DMF, $CH_2Cl_2$, and mixtures thereof. In a preferred embodiment, the reaction is conducted in dioxane at room temperature for a period of time between about 2 and 4 days.

Alternatively, the particles may be formed from polymers or blends of polymers with different polyester/amino acid backbones and grafted amino acid side chains. For example, poly(lactic acid-co-lysine-graft-alanine-lysine) (PLAL-Ala-Lys), or a blend of PLAL-Lys with poly(lactic acid-co-glycolic acid-block-ethylene oxide) (PLGA-PEG) (PLAL-Lys-PLGA-PEG) may be used.

In the synthesis, the graft copolymers may be tailored to optimize different characteristics of the aerodynamically light particle including: i) interactions between the agent to be delivered and the copolymer to provide stabilization of the agent and retention of activity upon delivery; ii) rate of polymer degradation and, thereby, rate of drug release profiles; iii) surface characteristics and targeting capabilities via chemical modification; and iv) particle porosity.

Therapeutic Agents

Any of a variety of therapeutic agents can be incorporated within the particles, which can locally or systemically deliver the incorporated agents following administration to the lungs of an animal. Examples include synthetic inorganic and organic compounds or molecules, proteins and peptides, polysaccharides and other sugars, lipids, and nucleic acid molecules having therapeutic, prophylactic or diagnostic activities. Nucleic acid molecules include genes, antisense molecules which bind to complementary DNA to inhibit transcription, ribozymes and ribozyme guide sequences. The agents to be incorporated can have a variety of biological activities, such as vasoactive agents, neuroactive agents, hormones, anticoagulants, immunomodulating agents, cytotoxic agents, prophylactic agents, antibiotics, antivirals, antisense, antigens, and antibodies. In some instances, the proteins may be antibodies or antigens which otherwise would have to be administered by injection to elicit an appropriate response. Compounds with a wide range of molecular weight, for example, between 100 and 500,000 grams per mole, can be encapsulated.

Proteins are defined as consisting of 100 amino acid residues or more; peptides are less than 100 amino acid residues. Unless otherwise stated, the term protein refers to both proteins and peptides. Examples include insulin and other hormones. Polysaccharides, such as heparin, can also be administered.

Aerosols including the aerodynamically light particles are useful for a variety of inhalation therapies. The particles can incorporate small and large drugs, release the incorporated drugs over time periods ranging from hours to months, and withstand extreme conditions during aerosolization or following deposition in the lungs that might otherwise harm the encapsulated agents.

The agents can be locally delivered within the lung or can be systemically administered. For example, genes for the treatment of diseases such as cystic fibrosis can be administered, as can beta agonists for asthma. Other specific therapeutic agents include insulin, calcitonin, leuprolide (or LHRH), G-CSF, parathyroid hormone-related peptide, somatostatin, testosterone, progesterone, estradiol, nicotine, fentanyl, norethisterone, clonidine, scopolomine, salicylate, cromolyn sodium, salmeterol, formeterol, albeterol, and valium.

Diagnostic Agents

Any of a variety of diagnostic agents can be incorporated within the particles, which can locally or systemically deliver the incorporated agents following administration to the lungs of an animal, including gases and other imaging agents.

Gases

Any biocompatible or pharmacologically acceptable gas can be incorporated into the particles or trapped in the pores of the particles. The term gas refers to any compound which is a gas or capable of forming a gas at the temperature at which imaging is being performed. The gas may be composed of a single compound such as oxygen, nitrogen, xenon, argon, nitrogen or a mixture of compounds such as air. Examples of fluorinated gases include $CF_4$, $C_2F_6$, $C_3F_8$, $C_4F_8$, $SF_6$, $C_2F_4$, and $C_3F_6$.

Other Imaging Agents

Other imaging agents which may be utilized include commercially available agents used in positron emission tomography (PET), computer assisted tomography (CAT), single photon emission computerized tomography, x-ray, fluoroscopy, and magnetic resonance imaging (MRI).

Examples of suitable materials for use as contrast agents in MRI include the gatalinium chelates currently available, such as diethylene triamine pentacetic acid (DTPA) and gatopentotate dimeglumine, as well as iron, magnesium, manganese, copper and chromium.

Examples of materials useful for CAT and x-rays include iodine based materials for intravenous administration, such as ionic monomers typified by diatrizoate and iothalamate, non-ionic monomers such as iopamidol, isohexol, and ioversol, non-ionic dimers, such as iotrol and iodixanol, and ionic dimers, for example, ioxagalte.

Particles incorporating these agents can be detected using standard techniques available in the art and commercially available equipment.

Formation of Aerodynamically Light Polymeric Particles

Aerodynamically light polymeric particles may be prepared using single and double emulsion solvent evaporation, spray drying, solvent extraction or other methods well known to those of ordinary skill in the art. The particles may be made, for example, using methods for making microspheres or microcapsules known in the art.

Methods for making microspheres are described in the literature, for example, in Mathiowitz and Langer, *J. Controlled Release* 5,13–22 (1987); Mathiowitz et al., *Reactive Polymers* 6, 275–283 (1987); and Mathiowitz et al., *J. Appl. Polymer Sci.* 35, 755–774 (1988). The selection of the method depends on the polymer selection, the size, external morphology, and crystallinity that is desired, as described, for example, by Mathiowitz et al., *Scanning Microscopy* 4,329–340 (1990); Mathiowitz et al., *J. Appl. Polymer Sci.* 45, 125–134 (1992); and Benita et al., *J. Pharm. Sci.* 73, 1721–1724 (1984).

In solvent evaporation, described for example, in Mathiowitz, et al., (1990), Benita, and U.S. Pat. No. 4,272,398 to Jaffe, a polymer is dissolved in a volatile organic solvent, such as methylene chloride. Several different polymer concentrations can be used, for example, between 0.05 and 0.20 g/ml. An agent to be incorporated, either in soluble form or dispersed as fine particles, is optionally added to the polymer solution, and the mixture is suspended in an aqueous phase that contains a surface active agent such as poly(vinyl alcohol). The resulting emulsion is stirred until most of the organic solvent evaporates, leaving solid microspheres, which may be washed with water and dried overnight in a lyophilizer.

Microspheres with different sizes (typically between 1 and 1000 microns) and morphologies can be obtained. This method is especially useful for relatively stable polymers such as polyesters and polystyrene. However, labile polymers such as polyanhydrides may degrade due to exposure to water. Solvent removal may be a preferred method for preparing microspheres from these polymers.

Solvent removal was primarily designed for use with polyanhydrides. In this method, a therapeutic or diagnostic agent can be dispersed or dissolved in a solution of a selected polymer in a volatile organic solvent like methylene chloride. The mixture can then be suspended in oil, such as silicon oil, by stirring, to form an emulsion. As the solvent diffuses into the oil phase, the emulsion droplets harden into solid polymer microspheres. Unlike solvent evaporation, this method can be used to make microspheres from polymers with high melting points and a wide range of molecular weights. Microspheres having a diameter between one and 300 microns can be obtained using this procedure.

Targeting of Particles

Targeting molecules can be attached to the particles via reactive functional groups on the particles. For example, targeting molecules can be attached to the amino acid groups of functionalized polyester graft copolymer particles, such as PLAL-Lys particles. Targeting molecules permit binding interactions of the particle with specific receptor sites, such as those within the lungs. The particles can be targeted by attaching ligands which specifically or non-specifically bind to particular targets. Exemplary targeting molecules include antibodies and fragments thereof including the variable regions, lectins, and hormones or other organic molecules capable of specific binding to receptors on the surfaces of the target cells.

Administration

The particles can be administered to the respiratory system alone or in any appropriate pharmaceutically acceptable carrier, such as a liquid, for example saline, or a powder. In one embodiment, particles incorporating a prophylactic, therapeutic or diagnostic agent are codelivered with larger carrier particles that do not include an incorporated agent. Preferably, the larger particles have a mass mean diameter between about 50 and 100 $\mu$m.

Aerosol dosage, formulations and delivery systems may be selected for a particular therapeutic application, as described, for example, in Gonda, I. "Aerosols for delivery of therapeutic and diagnostic agents to the respiratory tract," in *Critical Reviews in Therapeutic Drug Carrier Systems*, 6:273–313, 1990; and in Moren, "Aerosol dosage forms and formulations," in: *Aerosols in Medicine. Principles, Diagnosis and Therapy*, Moren, et al., Eds, Elsevier, Amsterdam, 1985.

The greater efficiency of aerosolization by aerodynamically light particles of relatively large size permits more of an incorporated agent to be delivered than is possible with the same mass of relatively dense aerosols. The relatively large particle size also minimizes potential drug losses caused by particle phagocytosis. When the particles are formed from biocompatible polymers, the system can provide controlled release in the lungs and long-time local action or systemic bioavailability of the incorporated agent. Denaturation of macromolecular drugs can be minimized during aerosolization since macromolecules are contained and protected within a polymeric shell. The enzymatic degradation of proteins or peptides can be minimized by co-incorporating peptidase-inhibitors.

Diagnostic Applications

The particles can be combined with a pharmaceutically acceptable carrier, then an effective amount for detection administered to a patient via inhalation. Particles containing an incorporated imaging agent may be used for a variety of diagnostic applications, including detecting and characterizing tumor masses and tissues.

The present invention will be further understood by reference to the following non-limiting examples.

EXAMPLE 1

Synthesis of Aerodynamically Light Poly[(p-carboxyphenoxy)-hexane anhydride] ("PCPH") Particles Aerodynamically light poly[(p-carboxyphenoxy)-hexane anhydride] ("PCPH") particles were synthesized as follows. 100 mg PCPH (MW approximately 25,000) was dissolved in 3.0 mL methylene chloride. To this clear solution was added 5.0 mL 1% w/v aqueous polyvinyl alcohol (PVA, MW approximately 25,000, 88 mole % hydrolyzed) saturated with methylene chloride, and the mixture was vortexed (Vortex Genie 2, Fisher Scientific) at maximum speed for one minute. The resulting milky-white emulsion was poured into a beaker containing 95 mL 1% PVA and homogenized (Silverson Homogenizers) at 6000 RPM for one minute using a 0.75 inch tip. After homogenization, the mixture was stirred with a magnetic stirring bar and the methylene chloride quickly extracted from the polymer particles by adding 2 mL isopropyl alcohol. The mixture was stirred for 35 minutes to allow complete hardening of the microparticles. The hardened particles were collected by centrifugation and washed several times with double distilled water. The particles were freeze dried to obtain a free-flowing powder void of clumps. Yield, 85–90%.

The mean diameter of this batch was 6.0 $\mu$m, however, particles with mean diameters ranging from a few hundred nanometers to several millimeters may be made with only slight modifications. Scanning electron micrograph photos of a typical batch of PCPH particles showed the particles to be highly porous with irregular surface shape. The particles had a tap density less than 0.4 g/cm$^3$.

EXAMPLE 2

Synthesis of PLAL-Lys and PLAL-Lys-Ala Polymeric and Copolymeric Particles

Aerodynamically Light PLAL-Lys Particles

PLAL-Lys particles were prepared by dissolving 50 mg of the graft copolymer in 0.5 ml dimethylsulfoxide, then adding 1.5 ml dichloromethane dropwise. The polymer solution is emulsified in 100 ml of 5% w/v polyvinyl alcohol solution (average molecular weight 25KDa, 88% hydrolyzed) using a homogenizer (Silverson) at a speed of approximately 7500 rpm. The resulting dispersion was stirred using a magnetic stirrer for 1 hour. Following this period, the pH was brought to between 7.0 and 7.2 by addition of a 0.1 N NaOH solution. Stirring was continued for an additional 2 hours until the dichloromethane was completely evaporated and the particles hardened. The particles were then isolated by centrifugation at 4000 rpm (1600 g) for 10 minutes (Sorvall RC-5 B). The supernatant was discarded and the precipitate washed three times with distilled water followed by centrifugation for 10 minutes at 4000 rpm each time. Finally, the particles were resuspended in 5 ml of distilled water, the dispersion frozen in liquid nitrogen, and lyophilized (Labconco freeze dryer 8) for at least 48 hours. Particle sizing was performed using a Coulter counter. Average particle mean diameters ranged from between 100 nm and 14 $\mu$m, depending upon processing parameters such as homogenization speed and time. All particles exhibited tap densities less than 0.4 g/cm$^3$. Scanning electron micrograph photos of the particles showed them to be highly porous with irregular surfaces.

Aerodynamically Light PLAL-Ala-Lys Particles 100 mg of PLAL-Ala-Lys was completely dissolved in 0.4 ml trifluoroethanol, then 1.0 ml methylene chloride was added dropwise. The polymer solution was emulsified in 100 ml of 1% w/v polyvinyl alcohol solution (average molecular weight 25 KDa, 80% hydrolyzed) using a sonicator (Sonic&Material VC-250) for 15 seconds at an output of 40 W. 2 ml of 1% PVA solution was added to the mixture and it was vortexed at the highest speed for 30 seconds. The mixture was quickly poured into a beaker containing 100 ml 0.3% PVA solution, and stirred for three hours allowing evaporation of the methylene chloride. Scanning electron micrograph photos of the particles showed them to possess highly irregular surfaces.

Aerodynamically Light Copolymer Particles

Polymeric aerodynamically light particles consisting of a blend of PLAL-Lys and PLGA-PEG were made. 50 mg of the PLGA-PEG polymer (molecular weight of PEG: 20 KDa, 1:2 weight ratio of PEG:PLGA, 75:25 lactide:glycolide) was completely dissolved in 1 ml dichloromethane. 3 mg of poly(lactide-co-lysine)-polylysine graft copolymer was dissolved in 0.1 ml dimethylsulfoxide and mixed with the first polymer solution. 0.2 ml of TE buffer, pH 7.6, was emulsified in the polymer solution by probe sonication (Sonic&Material VC-250) for 10 seconds at an output of 40W. To this first emulsion, 2 ml of distilled water was added and mixed using a vortex mixer at 4000 rpm for 60 seconds. The resulting dispersion was agitated by using a magnetic stirrer for 3 hours until methylene chloride was completely evaporated and microspheres formed. The spheres were then isolated by centrifugation at 5000 rpm for 30 min. The supernatant was discarded, the precipitate washed three times with distilled water and resuspended in 5 ml of water. The dispersion was frozen in liquid nitrogen and lyophilized for 48 hours.

By scanning electron microscopy (SEM), the PLAL-Lys-PLGAPEG particles were highly surface rough and porous. The particles had a mean particle diameter of 7 μm. The blend of PLAL-Lys with poly(lactic acid) (PLA) and/or PLGA-PEG copolymers can be adjusted to adjust particle porosity and size.

Variables which may be manipulated to alter the size distribution of the particles include: polymer concentration, polymer molecular weight, surfactant type (e.g., PVA, PEG, etc.), surfactant concentration, and mixing intensity. Variables which may be manipulated to alter the surface shape and porosity of the particles include: polymer concentration, polymer molecular weight, rate of methylene chloride extraction by isopropyl alcohol (or another miscible solvent), volume of isopropyl alcohol added, inclusion of an inner water phase, volume of inner water phase, inclusion of salts or other highly water-soluble molecules in the inner water phase which leak out of the hardening sphere by osmotic pressure, causing the formation of channels, or pores, in proportion to their concentration, and surfactant type and concentration.

Additionally, processing parameters such as homogenization speed and time can be adjusted. Neither PLAL, PLA nor PLGA-PEG alone yields an aerodynamically light structure when prepared by these techniques.

EXAMPLE 3

Synthesis of Spray-Dried Particles

Aerodynamically Light Particles Containing Polymer and Drug Soluble in Common Solvent Aerodynamically light 50:50 PLGA particles were prepared by spray drying with testosterone encapsulated within the particles according to the following procedures. 2.0 g poly (D,L-lactic-co-glycolic acid) with a molar ratio of 50:50 (PLGA 50:50, Resomer RG503, B.I. Chemicals, Montvale, N.J.) and 0.50 g testosterone (Sigma Chemical Co., St. Louis, Mo.) were completely dissolved in 100 mL dichloromethane at room temperature. The mixture was subsequently spray-dried through a 0.5 mm nozzle at a flow rate of 5 mL/min using a Buchi laboratory spraydrier (model 190, Buchi, Germany). The flow rate of compressed air was 700 nl/h. The inlet temperature was set to 30° C. and the outlet temperature to 25° C. The aspirator was set to achieve a vacuum of −20 to −25 bar. The yield was 51% and the mean particle size was approximately 5 μm. The particles were aerodynamically light, as determined by a tap density less than or equal to 0.4 g/cm$^3$.

Larger particle size can be achieved by lowering the inlet compressed air flow rate, as well as by changing other variables. Porosity and surface roughness can be increased by varying the inlet and outlet temperatures, among other factors.

Aerodynamically Light Particles Containing Polymer and Drug in Different Solvents Aerodynamically light PLA particles with a model hydrophilic drug (dextran) were prepared by spray drying using the following procedure. 2.0 mL of an aqueous 10% w/v FITC-dextran (MW 70,000, Sigma Chemical Co.) solution was emulsified into 100 mL of a 2% w/v solution of poly (D,L-lactic acid) (PLA, Resomer R206, B.I. Chemicals) in dichloromethane by probe sonication (Vibracell Sonicator, Branson). The emulsion was subsequently spray-dried at a flow rate of 5 mL/min with an air flow rate of 700 nl/h (inlet temperature=30° C., outlet temperature=21° C., −20 mbar vacuum). The yield is 56%. The particles were aerodynamically light (tap density less than 0.4 g/cm$^3$).

Aerodynamically Light Protein Particles

Aerodynamically light lysozyme particles were prepared by spray drying using the following procedure. 4.75 g lysozyme (Sigma) was dissolved in 95 mL double distilled water (5% w/v solution) and spray-dried using a 0.5 mm nozzle and a Buchi laboratory spray-drier. The flow rate of compressed air was 725 nl/h. The flow rate of the lysozyme solution was set such that, at a set inlet temperature of 97–100° C., the outlet temperature is between 55 and 57° C. The aspirator was set to achieve a vacuum of −30 mbar. The enzymatic activity of lysozyme was found to be unaffected by this process and the yield of the aerodynamically light particles (tap density less than 0.4 g/cm$^3$) was 66%.

Aerodynamically Light High-Molecular Weight Water-Soluble Particles

Aerodynamically light dextran particles were prepared by spray drying using the following procedure. 6.04 g DEAE dextran (Sigma) was dissolved in 242 mL double distilled water (2.5% w/v solution) and spray-dried using a 0.5 mm nozzle and a Buchi laboratory spray-drier. The flow rate of compressed air was 750 nl/h. The flow rate of the DEAE-dextran solution was set such that, at a set inlet temperature of 155° C., the outlet temperature was 80° C. The aspirator was set to achieve a vacuum of −20 mbar. The yield of the aerodynamically light particles (tap density less than 0.4 g/cm$^3$) was 66% and the size range ranged between 1 and 15 μm.

Aerodynamically Light Low-Molecular Weight Water-Soluble Particles

Aerodynamically light trehalose particles were prepared by spray drying using the following procedure. 4.9 g trehalose (Sigma) was dissolved in 192 mL double distilled water (2.5% wlv solution) and spray-dried using a 0.5 mm nozzle and a Buchi laboratory spray-drier. The flow rate of compressed air 650 nl/h. The flow rate of the trehalose solution was set such that, at a set inlet temperature of 100° C., the outlet temperature was 60° C. The aspirator was set to achieve a vacuum of -30 mbar. The yield of the aerodynamically light particles (tap density less than 0.4 g/cm$^3$) was 36% and the size range ranged between 1 and 15 µm.

Aerodynamically Light Low-Molecular Weight Water-Soluble Particles

Polyethylene glycol (PEG) is a water-soluble macromolecule, however, it cannot be spray dried from an aqueous solution since it melts at room temperatures below that needed to evaporate water. PEG was spray-dried at low temperatures from a solution in dichloromethane, a low boiling organic solvent. Aerodynamically light PEG particles were prepared by spray drying using the following procedure. 5.0 g PEG (MW 15,000–20,000, Sigma) was dissolved in 100 mL double distilled water (5.0% w/v solution) and spray-dried using a 0.5 mm nozzle and a Buchi laboratory spray-drier. The flow rate of compressed air was 750 nl/h. The flow rate of the PEG solution was set such that, at a set inlet temperature of 45° C., the outlet temperature was 34–35° C. The aspirator was set to achieve a vacuum of -22 mbar. The yield of the aerodynamically light particles (tap density less than 0.4 g/cm$^3$) was 67% and the size range ranged between 1 and 15 µm.

EXAMPLE 4

Rhodamine Isothiocyanate Labeling of PLAL and PLAL-Lys Particles

Aerodynamically light particles were compared with control particles, referred to herein as "non-light" particles. Lysine amine groups on the surface of aerodynamically light (PLAL-Lys) and control, non-light (PLAL) particles, with similar mean diameters (between 6 and 7 µm) and size distributions (standard deviations between 3 and 4 µm) were labeled with Rhodamine isothiocyanate. The tap density of the porous PLAL-Lys particles was 0.1 g/cm$^3$ and that of the denser PLAL particles was 0.8 g/cm$^3$.

The rhodamine-labeled particles were characterized by confocal microscopy. A limited number of lysine functionalities on the surface of the solid particle were able to react with rhodamine isothiocyanate, as evidenced by the fluorescent image. In the aerodynamically light particle, the higher lysine content in the graft copolymer and the porous particle structure result in a higher level of rhodamine attachment, with rhodamine attachment dispersed throughout the interstices of the porous structure. This also demonstrates that targeting molecules can be attached to the aerodynamically light particles for interaction with specific receptor sites within the lungs via chemical attachment of appropriate targeting agents to the particle surface.

EXAMPLE 5

Aerosolization of PLAL and PLAL-Lys Particles

To determine whether large aerodynamically light particles can escape (mouth, throat and inhaler) deposition and more efficiently enter the airways and acini than nonporous particles of similar size (referred to herein as non-light or control particles), the aerosolization and deposition of aerodynamically light PLAL-Lys (mean diameter 6.3 µm) and control, non-light PLAL (mean diameter 6.9 µm) particles was compared in vitro using a cascade impactor system.

20 mg of the aerodynamically light or non-light microparticles were placed in gelatine capsules (Eli Lilly), the capsules loaded into a Spinhaler dry powder inhaler (DPI) (Fisons), and the DPI activated. Particles were aerosolized into a Mark I Andersen Impactor (Andersen Samplers, Ga.) from the DPI for 30 seconds at 28.3 l/min flow rate. Each plate of the Andersen Impactor was previously coated with Tween 80 by immersing the plates in an acetone solution (5% w/vol) and subsequently evaporating the acetone in a oven at 60° C. for 5 min. After aerosolization and deposition, particles were collected from each stage of the impactor system in separate volumetric flasks by rinsing each stage with a NaOH solution (0.2 N) in order to completely degrade the polymers. After incubation at 37° C. for 12 h, the fluorescence of each solution was measured (wavelengths of 554 nm excitation, 574 nm emission).

Figure 1:
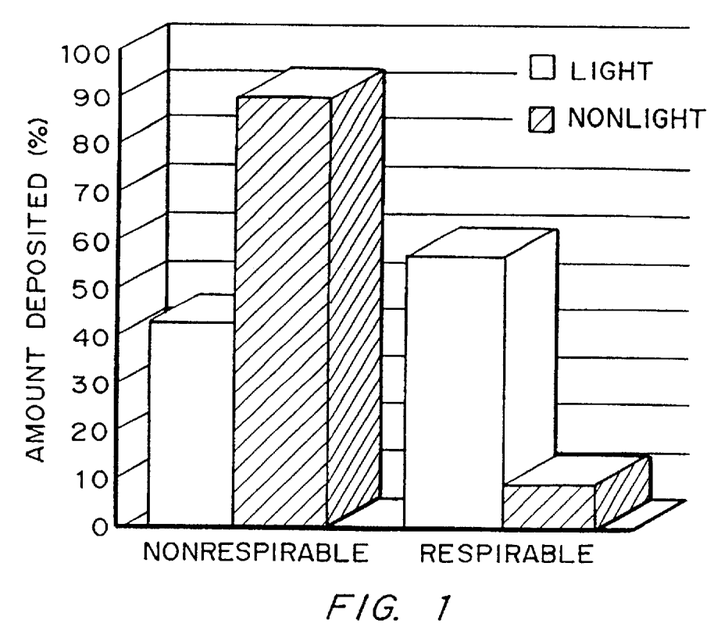
FIG. 1 is a graph comparing total particle mass of aerodynamically light and non-light, control particles deposited on the nonrespirable and respirable stages of a cascade impactor following aerosolization.

Particles were determined as nonrespirable (mean aerodynamic diameter exceeding 4.7 µm: impactor estimate) if they deposited on the first three stages of the impactor, and respirable (mean aerodynamic diameter 4.7 µm or less) if they deposited on subsequent stages. FIG. 1 shows that less than 10% of the non-light (PLAL) particles that exit the DPI are respirable. This is consistent with the large size of the microparticles and their standard mass density. On the other hand, greater than 55% of the aerodynamically light (PLAL-Lys) particles are respirable, even though the geometrical dimensions of the two particle types are almost identical. The lower tap density of the aerodynamically light (PLAL-Lys) microparticles is responsible for this improvement in particle penetration, as discussed further below.

The non-light (PLAL) particles also inefficiently aerosolize from the DPI; typically, less than 40% of the non-light particles exited the Spinhaler DPI for the protocol used. The aerodynamically light (PLAL-Lys) particles exhibited much more efficient aerosolization (approximately 80% of the aerodynamically light microparticles typically exited the DPI during aerosolization).

The combined effects of efficient aerosolization and high respirable fraction of aerosolized particle mass means that a far greater fraction of an aerodynamically light particle powder is likely to deposit in the lungs than of a non-light particle powder.

EXAMPLE 6

In Vivo Aerosolization of PLAL and PLAL-Lys Particles

The penetration of aerodynamically light and non-light polymeric PLAL-Lys and PLAL microparticles into the lungs was evaluated in an in vivo experiment involving the aerosolization of the microparticles into the airways of live rats.

Male Spraque Dawley rats (150–200 g) were anesthetized using ketamine (90 mg/kg)/xylazine (10 mg/kg). The anesthetized rat was placed ventral side up on a surgical table provided with a temperature controlled pad to maintain physiological temperature. The animal was cannulated above the carina with an endotracheal tube connected to a Harvard ventilator. The animal was force ventilated for 20 minutes at 300 ml/min. 50 mg of aerodynamically light (PLAL-Lys) or non-light (PLA) microparticles were introduced into the endotracheal tube.

Figure 2:
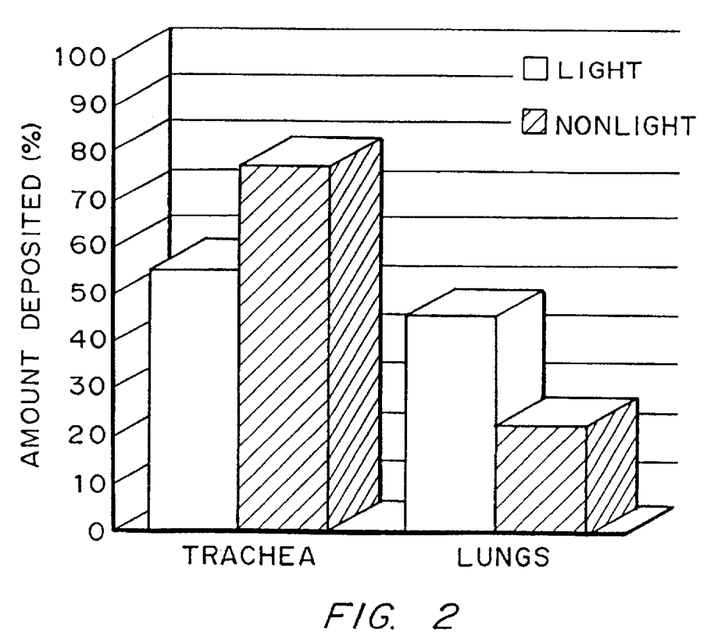
FIG. 2 is a graph comparing total particle mass deposited in the trachea and after the carina (lungs) in rat lungs and upper airways following intratracheal aerosolization during forced ventilation of aerodynamically light poly(lactic acid-co-lysine-graft-lysine) (PLAL-Lys) particles and control, non-light poly(L-lactic acid) (PLA) particles.

Following the period of forced ventilation, the animal was euthanized and the lungs and trachea were separately washed using bronchoalveolar lavage. A tracheal cannula was inserted, tied into place, and the airways were washed with 10 ml aliquots of HBSS. The lavage procedure was repeated until a total volume of 30 ml was collected. The lavage fluid was centrifuged (400 g) and the pellets collected and resuspended in 2 ml of phenol red-free Hanks balanced salt solution (Gibco, Grand Island, N.Y.) without $Ca^2$ and $Mg^{2+}$ (HBSS). 100 ml were removed for particle counting using a hemacytometer. The remaining solution was mixed with 10 ml of 0.4 N NaOH. After incubation at 37° C. for 12 h, the fluorescence of each solution was measured (wavelengths of 554 nm excitation, 574 nm emission). FIG. 2 is a bar graph showing total particle mass deposited in the trachea and after the carina (lungs) in rat lungs and upper airways following intratracheal aerosolization during forced ventilation. The PLAL-Lys aerodynamically light particles had a mean diameter of 6.9 $\mu$m. The non-light PLAL particles had a mean diameter of 6.7 $\mu$m. Percent tracheal aerodynamically light particle deposition was 54.5, and non-light deposition was 77.0. Percent aerodynamically light particle deposition in the lungs was 46.8 and non-light deposition was 23.0.

The non-light (PLAL) particles deposited primarily in the trachea (approximately 79% of all particle mass that entered the trachea). This result is similar to the in vitro performance of the non-light microparticles and is consistent with the relatively large size of the nonlight particles. Approximately 54% of the aerodynamically light (PLAL-Lys) particle mass deposited in the trachea. Therefore, about half of the aerodynamically light particle mass that enters the trachea traverses through the trachea and into the airways and acini of the rat lungs, demonstrating the effective penetration of the aerodynamically light particles into the lungs.

Figure 3:
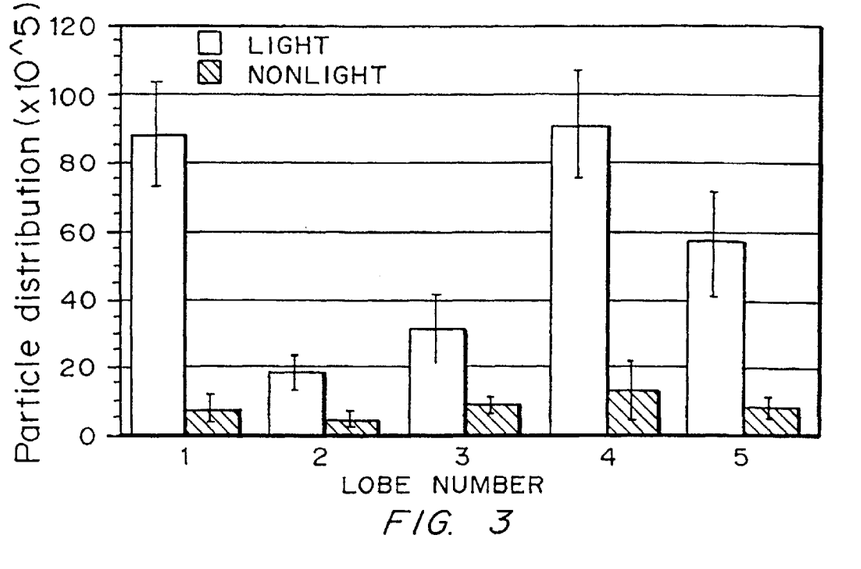
FIG. 3 is a graph comparing total particle recovery of aerodynamically light PLAL-Lys particles and control PLA particles in rat lungs following bronchoalveolar lavage.

Following bronchoalveolar lavage, particles remaining in the rat lungs were obtained by careful dissection of the individual lobes of the lungs. The lobes were placed in separate petri dishes containing 5 ml of HBSS. Each lobe was teased through 60 mesh screen to dissociate the tissue and was then filtered through cotton gauze to remove tissue debris and connective tissue. The petri dish and gauze were washed with an additional 15 ml of HBSS to maximize microparticle collection. Each tissue preparation was centrifuged and resuspended in 2 ml of HBSS and the number of particles counted in a hemacytometer. The particle numbers remaining in the lungs following the bronchoalveolar lavage are shown in FIG. 3. Lobe numbers correspond to: 1) left lung, 2) anterior, 3) median, 4) posterior, 5) postcaval. A considerably greater number of aerodynamically light PLAL-Lys particles enters every lobe of the lungs than the nonlight PLAL particles, even though the geometrical dimensions of the two types of particles are essentially the same. These results reflect both the efficiency of aerodynamically light particle aerosolization and the propensity of the aerodynamically light particles to escape deposition prior to the carina or first bifurcation.

EXAMPLE 7

Figure 4:
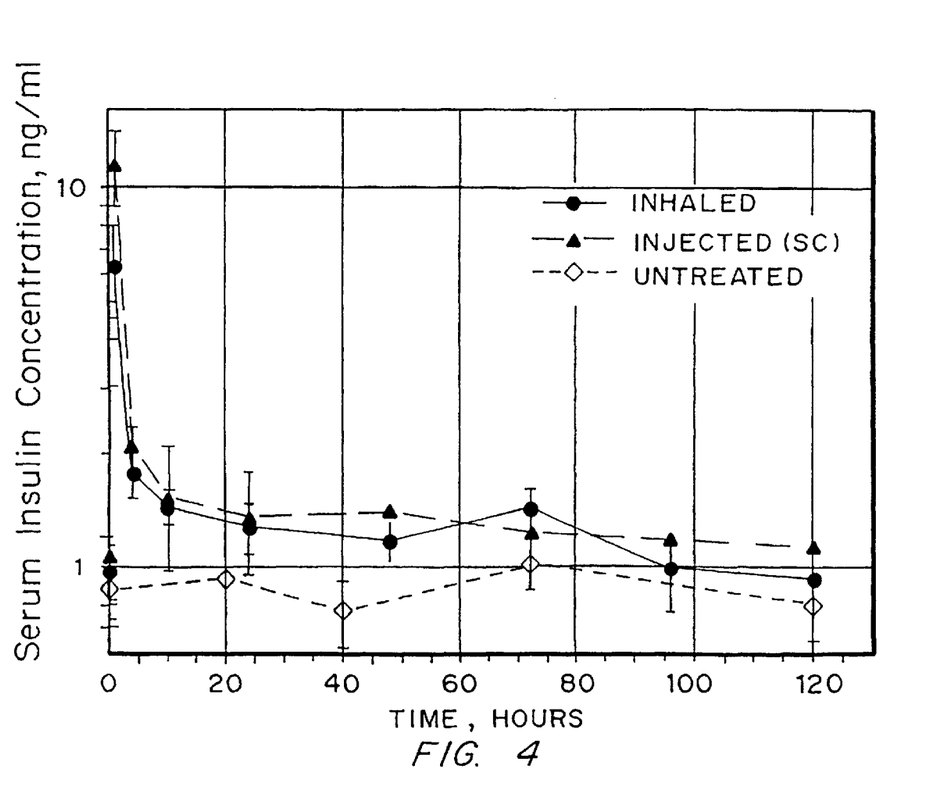
FIG. 4 is a graph representing serum insulin levels (ng/ml) over time (hours) following administration via inhalation or subcutaneous injection of porous PLGA particles.
Figure 5:
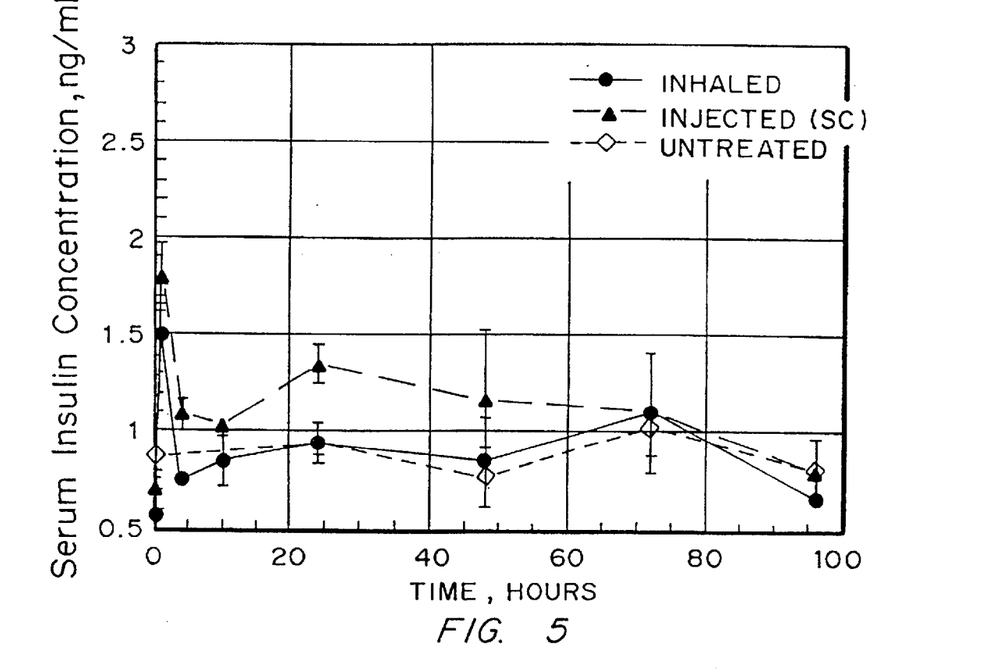
FIG. 5 is a graph representing serum insulin levels (ng/ml) over time (hours) following administration via inhalation or subcutaneous injection of non-porous PLGA particles. Darkened circles represent administration via inhalation. Darkened triangles represent administration via subcutaneous injection. Empty diamonds represent untreated controls.

In Vivo Aerosolization of PLGA Porous and Non-Porous Particles Including Insulin Insulin was encapsulated into porous and nonporous polymeric particles to test whether large particle size can increase systemic bioavailability. The mass densities and mean diameters of the two particles were designed such that they each possessed an aerodynamic diameter (approximately 2 $\mu$m) suitable for deep lung deposition, with the mean diameter of the porous particles >5 $\mu$m and that of the nonporous particles less than 5 $\mu$m (see FIGS. 4–6). Identical masses of the porous or nonporous particles were administered to rats as an inhalation aerosol or injected subcutaneously (controls).

Rats were anesthetized and cannulated as previously described. The animal was force ventilated for between 10 and 20 minutes at 300 ml/min. Two types of aerosols were delivered to the animal via the endotracheal tube. Following the period of forced ventilation, the neck of the animal was sutured and the animal revived within one to two hours. Blood samples (300 $\mu$l) were periodically withdrawn from the tail vein over a period of two to six days. These samples were mixed with assay buffer, centrifuged, and the supernatant examined for the presence of (endogenous and exogenous) insulin or testosterone using radioimmunoassays (ICN Pharmaceuticals, Costa Mesa, Calif.). Glucose was measured using a colorimetric assay (Sigma). Control studies involved subcutaneous injection of the same amount of powder as was inhaled. The particles were injected into the scruff of the neck.

Serum insulin concentrations were monitored as a function of time following inhalation or injection. For both porous (FIG. 4) and nonporous (FIG. 5) particles, blood levels of insulin reach high values within the first hour following inhalation. Only in the case of the large porous particles do blood levels of insulin remain elevated ($p<0.05$) beyond 4 h, with a relatively constant insulin release continuing to at least 96 h ($0.04<p<0.2$).

Figure 6:
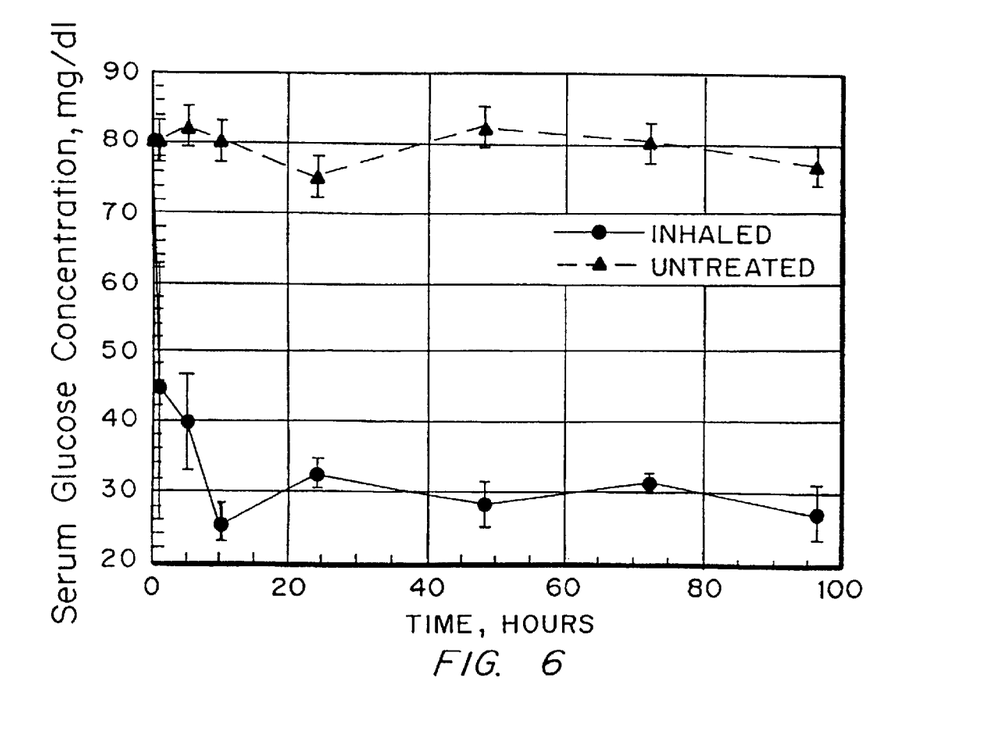
FIG. 6 is a graph representing serum glucose concentrations (mg/dl) following administration of porous PLGA particles via inhalation. Darkened circles represent administration via inhalation. Darkened triangles represent untreated controls.
Figure 7:
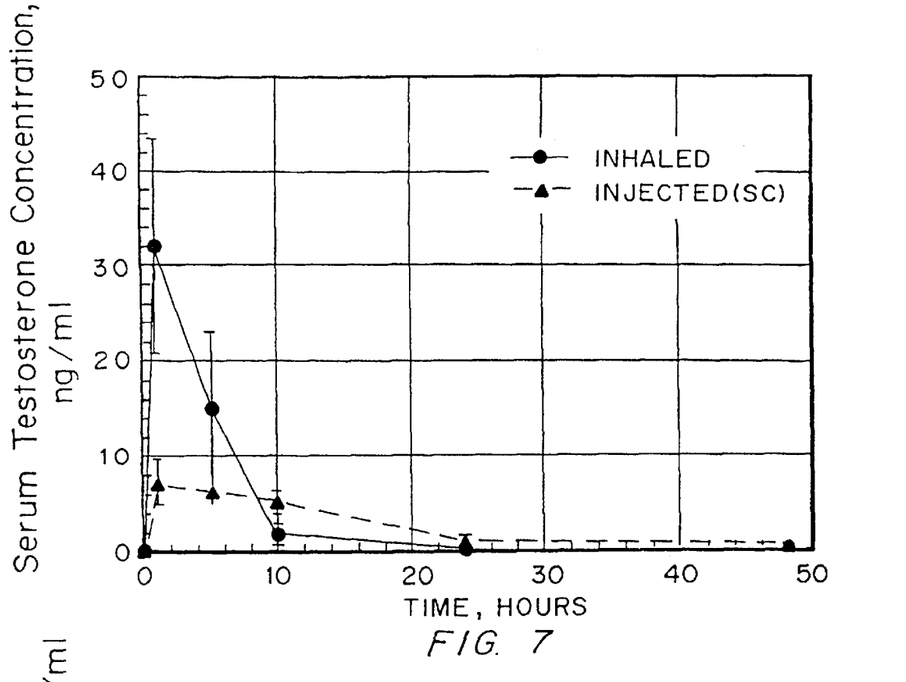
FIG. 7 is a graph representing serum testosterone levels (ng/ml) over time (hours) following administration via inhalation or subcutaneous injection of porous PLGA particles with a diameter of 20.4 $\mu$m. Darkened circles represent administration via inhalation. Darkened triangles represent administration via subcutaneous injection.
Figure 8:
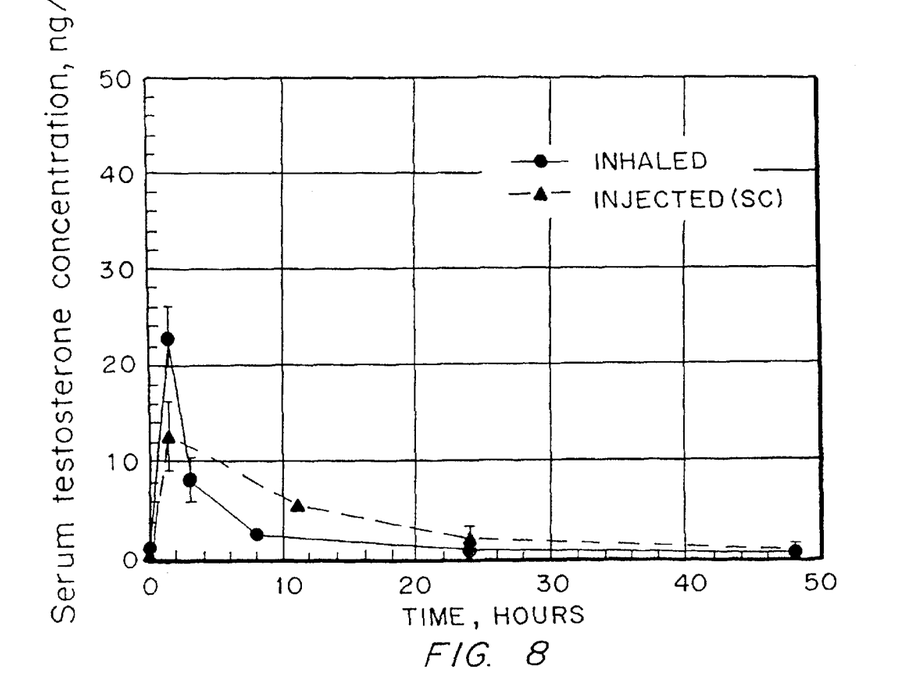
FIG. 8 is a graph representing serum testosterone levels (ng/ml) over time (hours) following administration via inhalation or subcutaneous injection of porous PLGA particles with a diameter of 10.1 $\mu$m. Darkened circles represent administration via inhalation. Darkened triangles represent administration via subcutaneous injection.

These results are confirmed by serum glucose values which show falling glucose levels for the first 10 h after inhalation of the porous insulin particles, followed by relatively constant low glucose levels for the remainder of the 96 h period, as shown in FIG. 6. In the case of small nonporous insulin particles, initially suppressed glucose values rose after 24 h.

Similar biphasic release profiles of macromolecules from PLGA polymers have been reported in the literature (S. Cohen et al. *Pharm. Res.* 8, 713 (1991)). For the large porous particles, insulin bioavailability relative to subcutaneous injection is 87.5%, whereas the small nonporous particles yield a relative bioavailability of 12% following inhalation. By comparison, bioavailability (relative to subcutaneous injection) of insulin administered to rats as an inhalation liquid aerosol using a similar endotracheal method has been reported as 37.3% (P. Colthorpe et al. *Pharm. Res.* 9, 764 (1992)). Absolute bioavailability of insulin inhaled into rat lungs in the form of a lactose/insulin powder via a dry powder inhaler connected to an endotracheal tube has been reported as 6.5% (F. Komada et al. *J. Phann. Sci.* 83, 863 (1994)).

Given the short systemic half life of insulin (11 minutes), and the 12–24 h time scale of particle clearance from the central and upper airways, the appearance of exogenous insulin in the bloodstream several days following inhalation appears to indicate that large porous particles achieve long, non-phagocytosed life-times when administered to the deep lung. To test this hypothesis, the lungs of rats were lavaged both inunediately following inhalation of the porous and nonporous insulin particles, and 48 h after inhalation.

In the case of nonporous particles, 30%±3% of phagocytic cells contained particles immediately following inhalation, and 39% ±5% contained particles 48 h after inhalation. By contrast only 8%±2% of phagocytic cells contained large porous particles right after inhalation, and 12.5%±13.5% contained particles 48 h after inhalation. In the small nonporous particle case, 17.5%±1.5% of the phagocytic cell population contained 3 or more particles 48 h after inhalation. compared to 4%±1% in the case of the large nonporous particles. Inflammatory response was also elevated in the small nonporous particle case; neutrophils represented 34%±12% of the phagocytic cell population 48 h following inhalation of the small nonporous particles, compared to 8.5%±3.5% in the large porous particle case (alveolar macrophages represented 100% of phagocytic cells immediately following inhalation). These results support in vitro experimental data appearing elsewhere that show phagocytosis of particles diminishes precipitously as particle diameter increases beyond 3μm (H. Kawaguchi, et al. *Biomaterials* 7, 61 (1986). L. J. Krenis, and B. Strauss, *Proc. Soc. Exp. Med.* 107, 748 (1961). S. Rudt, and R. H. Muller, *J. Contr. Rel.* 22, 263 (1992)).

EXAMPLE 8

In Vivo Aerosolization of PLGA Porous Particles Including Testosterone

A second model drug, testosterone, was encapsulated in porous particles of two different mean geometric diameters (10.1 μm and 20.4 μm) to further determine whether increased bioavailability correlates with increasing size of porous particles. An identical mass of powder was administered to rats as an inhalation aerosol or as a subcutaneous injection (controls). Serum testosterone concentrations were monitored as a function of time following inhalation or injection (FIGS. 7 and 8). Blood levels of testosterone remain well above background levels ($p<0.05$) for between 12 and 24 h, even though the systemic half-life of testosterone is between 10 and 20 minutes. Testosterone bioavailability relative to subcutaneous injection is 177% for the 20.4 μm diameter particles (FIG. 7) and 53% for the 10.1 μm diameter porous particles (FIG. 8).

The increase in testosterone bioavailability with increasing size of porous particles is especially notable given that the mean diameter of the 20.4 μm particles is approximately ten times larger than that of nonporous conventional therapeutic particles (D. Ganderton, *J. Biopharmaceutical Sciences* 3, 101 (1992). The relatively short time scale of testosterone release observed both for the inhalation and subcutaneous controls is near the several hour in vitro time scale of release reported elsewhere for 50:50 PLGA microparticles of similar size encapsulating a therapeutic substance (bupivacaine) of similar molecular weight and lipophilicity (P.-Le Corre et al. Int. *J. Pharm.* 107, 41 (1994)).

By making particles with high porosity, relatively large particles (i.e., those possessing the same aerodynamic diameter as smaller, nonporous particles) can enter the lungs, since it is particle mass that dictates location of aerosol deposition in the lungs. The increased aerosolization efficiency of large, light particles lowers the probability of deposition losses prior to particle entry into the airways, thereby increasing the systemic bioavailability of an inhaled drug.

What is claimed is:

1. A particulate system for delivery to the pulmonary system comprising particles which comprise a biodegradable material and a therapeutic, prophylactic or diagnostic agent, have a tap density of less than 0.4 $g/cm^3$ and a mass mean diameter between about 5 μm and about 30 μm.

2. The particulate system of claim 1 wherein the particles have an aerodynamic diameter less than about 5 μm.

3. The particulate system of claim 1 wherein the biodegradable material is a polymer.

4. The particulate system of claim 1 wherein the biodegradable material is a polysaccharide.

5. The particulate system of claim 1 wherein the agent is a hormone.

6. The particulate system of claim 5 wherein the agent is insulin.

7. The particulate system of claim 1 wherein the agent is an antibody.

8. The particulate system of claim 1 wherein the agent is estradiol.

9. The particulate system of claim 1 wherein the agent is a beta agonist.

10. The particlulate system of claim 1 wherein the agent is salicylate.

11. The particulate system of claim 1 wherein the agent is leuprolide.

12. The particulate system of claim 1 wherein the agent is somatostin.

13. A particulate system for delivery to the pulmonary system comprising particles which comprise a biodegradable material and a therapeutic, prophylactic or diagnostic agent, and wherein at least 90% of the particles have a tap density of less than 0.4 $g/cm^3$, and a mass mean particle diameter between about 5 μm and about 30 μm.

14. A particulate system for delivery to the pulmonary system comprising particles which comprise a biodegradable material and a therapeutic, prophylactic or diagnostic agent, have a tap density less than 0.1 $g/cm^3$ and a mass mean diameter between about 5 μm and about 30 μm.

15. A particulate system for delivery to the pulmonary system comprising particles which comprise a biodegradable material and a therapeutic, prophylactic or diagnostic agent, have an envelope mass density of less than 0.4 $g/cm^3$, and a particle diameter between about 5 μm and about 30 μm.

16. A method for delivering particles to the pulmonary system comprising administering to the respiratory tract of a patient in need of treatment, diagnosis or prophylaxis, an effective amount of particles which comprise a biodegradable material and a therapeutic, prophylactic or diagnostic agent, wherein the particles have a tap density of less than 0.4 $g/cm^3$ and a mass mean diameter between about 5 μm and about 30 μm.

17. The method of claim 16 wherein the particles have an aerodynamic diameter less than about 5 μm.

18. The method of claim 16 wherein the biodegradable material is a polymer.

19. The method of claim 16 wherein the biodegradable material is a polysaccharide.

20. The method of claim 16 wherein the agent is a hormone.

21. The method of claim 20 wherein the agent is insulin.

22. The method of claim 16 wherein the agent is an antibody.

23. The particulate system of claim 16 wherein the agent is estradiol.

24. The method of claim 16 wherein the agent is a beta agonist.

25. The method of claim 16 wherein the agent is salicylate.

26. The method of claim 16 wherein the agent is leuprolide.

27. The method of claim 16 wherein the agent is somatostin.

28. The method of claim 16 wherein delivery is to the deep lung.

29. The method of claim 16 wherein delivery is to the airways.

30. The method of claim 16 wherein the particles are administered through a dry powder inhaler.

31. The method of claim 16 wherein the particles biodegrade within the pulmonary system thereby releasing the agent at a controlled rate.

32. The method of claim 16 wherein the particles are administered in combination with a pharmaceutically acceptable carrier.

33. A method for delivering particles to the pulmonary system comprising administering to the respiratory system of a patient in need of treatment, prophylaxis or diagnosis an effective amount of particles which comprise a biodegradable material and a therapeutic, prophylactic or diagnostic agent, wherein at least 90% of the particles have a tap density of less than 0.4 g/$cm^3$, and a mass mean diameter between about 5 $\mu$m and about 30 $\mu$m.

34. A method for delivering particles to the pulmonary system comprising administering to the respiratory system of a patient in need of treatment, prophylaxis or diagnosis an effective amount of particles which comprise a biodegradable material and a therapeutic, prophylactic or diagnostic agent, wherein the particles have a tap density of less than 0.1 g/$cm^3$, and a mass mean diameter between about 5 $\mu$m and about 30 $\mu$m.

35. A method for delivering particles to the pulmonary system comprising administering to the respiratory system of a patient in need of treatment, prophylaxis or diagnosis an effective amount of particles which comprise a biodegradable material and a therapeutic, prophylactic or diagnostic agent, wherein the particles have an envelope mass density of less than 0.4 g/$cm^3$, and a particle diameter between about 5 $\mu$m and about 30 $\mu$m.

* * * * *